United States Patent
Treusch (12)

(10) Patent No.: US 6,448,227 B1
(45) Date of Patent: Sep. 10, 2002

(54) THERAPEUTICALLY EFFECTIVE SUBSTANCE MIXTURE

(76) Inventor: Gernot Treusch, Empuria Erava, Falconera 59, Castello d'Empories (ES)

( * ) Notice: Subject to any disclaimer, the term of this patent is extended or adjusted under 35 U.S.C. 154(b) by 0 days.

(21) Appl. No.: 09/913,935

(22) PCT Filed: Feb. 22, 2000

(86) PCT No.: PCT/EP00/01419

§ 371 (c)(1),
(2), (4) Date: Aug. 20, 2001

(87) PCT Pub. No.: WO00/50060

PCT Pub. Date: Aug. 31, 2000

(30) Foreign Application Priority Data

Feb. 22, 1999 (DE) .......................... 199 07 507

(51) Int. Cl.⁷ .......................... A61K 38/00; A61K 31/52
(52) U.S. Cl. .......................... 514/18; 514/262
(58) Field of Search .................. 514/18, 262

(56) References Cited

FOREIGN PATENT DOCUMENTS

| GB | 761 09 3 A | 11/1956 |
| WO | 92 03 146 | 3/1992 |

OTHER PUBLICATIONS

O'Brien W J et al: "Effects of nucleoside antivirals and their metabolites on the corneal endothelium." Current Eye Research, (1981) 1 (4) 243–8.

Kurokawa M et al: "Efficacy of Traditional Herbal Medicines in Combination with Acyclovir Against Herpes Simplex Virus Type 1 Infection In Vitro and In Vivo" Antiviral Research, NL, Elsevier Science BV., Amsterdam, Bd. 27, Nr. 1/02, 1995, pp. 19–37.

Pancheva S. et al: "Effect of combined acyclovir and ribavirin on experimental Herpes simplex virus type 1 keratoconjunctivitis in rabbits" Acta Microbiologica Bulgarica, Bd. 29, 1993, pp. 61–64, XP000911006.

Mucsi I et al: "Combined Effects of Flavonoids and Acyclovir Against Herpesviruses in Cell Cultures" Acta Microbiologica Hungarica, Hu, Akad. Kiado, Budapest, Bd. 39, Nr. 2, 1992, pp. 137–147.

Holliday J et al: "Inhibition of herpes simplex virus types 1 and 2 replication in vitro by mercurithio analogs of deoxyuridine." Antiviral Research, (Sep. 1991) 16 (2) 197–203.

Field H J et al: "Effect of Acycloguanosine Treatment on Acute and Latent Herpes Simplex Infections in Mice" Antimicrobial Agents and Chemotherapy, US, American Society for Microbiology, Washington, DC, Bd. 15, Nr. 4, Apr. 1, 1979 pp. 554–561, XP000568622.

Primary Examiner—Raymond Henley, III
(74) Attorney, Agent, or Firm—Milton M. Field

(57) ABSTRACT

A substance mixture, containing S-acetyl glutathione and Aciclovir, is effective as a medication against the Herpes Simplex virus and the Varicella Zoster virus.

2 Claims, 2 Drawing Sheets

THERAPEUTICALLY EFFECTIVE SUBSTANCE MIXTURE

This is a 371 of PCT/EP00/01419 filed Feb. 22, 2000. From European patent 0 327 612 B1, the use is known of S-acetyl glutathione as a medical substance with various different indications. S-acetyl glutathione is the monoacetyl-(thio)-ester of glutathione (gamma-glutamyl-cysteinyl-glycine) with the following structure formula:

BACKGROUND OF THE INVENTION

1. Field of the Invention

This invention relates to a mixture containing S-acetyl glutathione and Aciclovir (ACV) as medication against the Herpes Simplex virus or the Varicella Zoster virus.

2. Description of the Prior Art

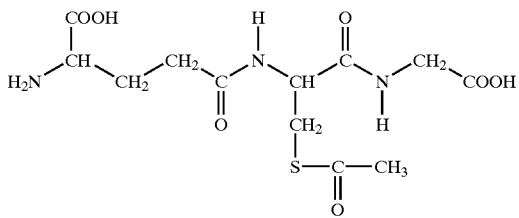

A process for the manufacture of S-acetyl glutathione is disclosed in U.S. Pat No. 2,760,956.

Aciclovir (ACV) is a known medication for use against the Herpes Simplex virus (HSV). Aciclovir is an abbreviated nomenclature (INN) for 9-[(2-hydroxyethoxy)methyl] guanine.

SUMMARY THE INVENTION

It has now been recognized that, surprisingly, the combination of S-acetyl glutathione and ACV has a strong synergetic effect against the Herpes Simplex virus (HSV), especially against HSV-1, as well as against the Varicella Zoster virus (VZV).

In-vitro experiments were conducted as to the influence of S-acetyl glutathione and Aciclovir (ACV), in each case individually and in combination with one another, on HSV-1 replication in human foreskin fibroblasts with MEM plus 10% foetal calf serum as the medium. In this situation, two different concentrations of S-acetyl glutathione and three different concentrations of ACV were used. The results are shown in Table 1.

S-acetyl glutathione is effective against HSV-1 from a concentration of 10 mM (millimole/liter). ACV alone shows, as expected, a clear effectiveness, especially in the concentration of 2 $\mu$M (micromole/liter). The combination of S-acetyl glutathione and ACV results in a strongly synergistic anti-HSV-1 effect. If S-acetyl glutathione is applied in a concentration of 20 mM together with ACV in a concentration of 2 $\mu$M, no further virus titer can be demonstrated.

Figure 1A:
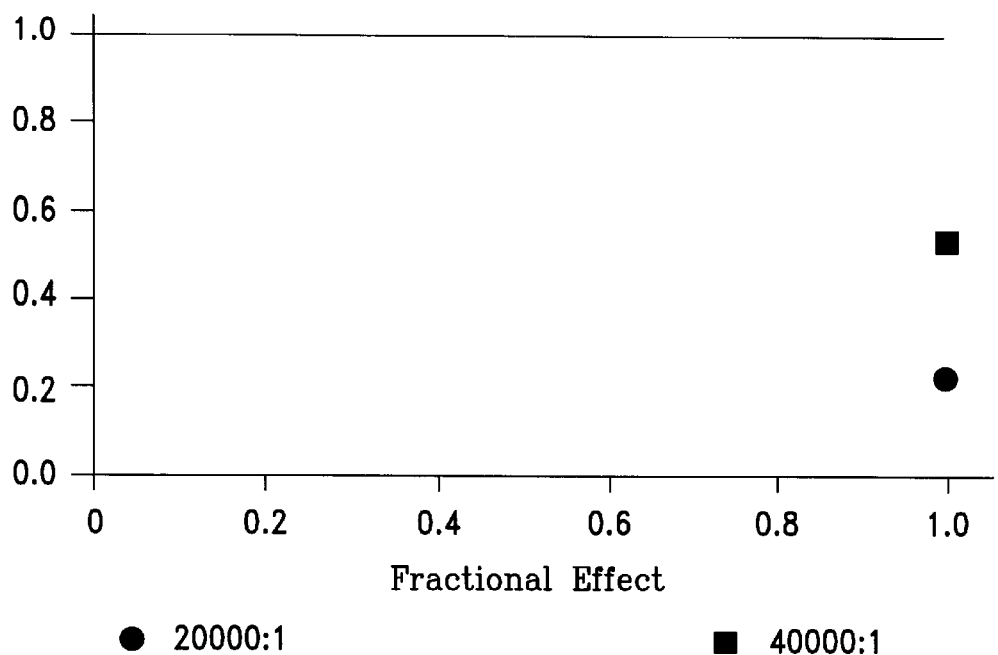
FIGS. 1A and 1B are diagrams showing the results of in-vitro experiments as to the influence of S-acetyl glutathione and Aciclovir (ACV) on HSV-1 virus on human foreskin fibroblasts.
Figure 1B:
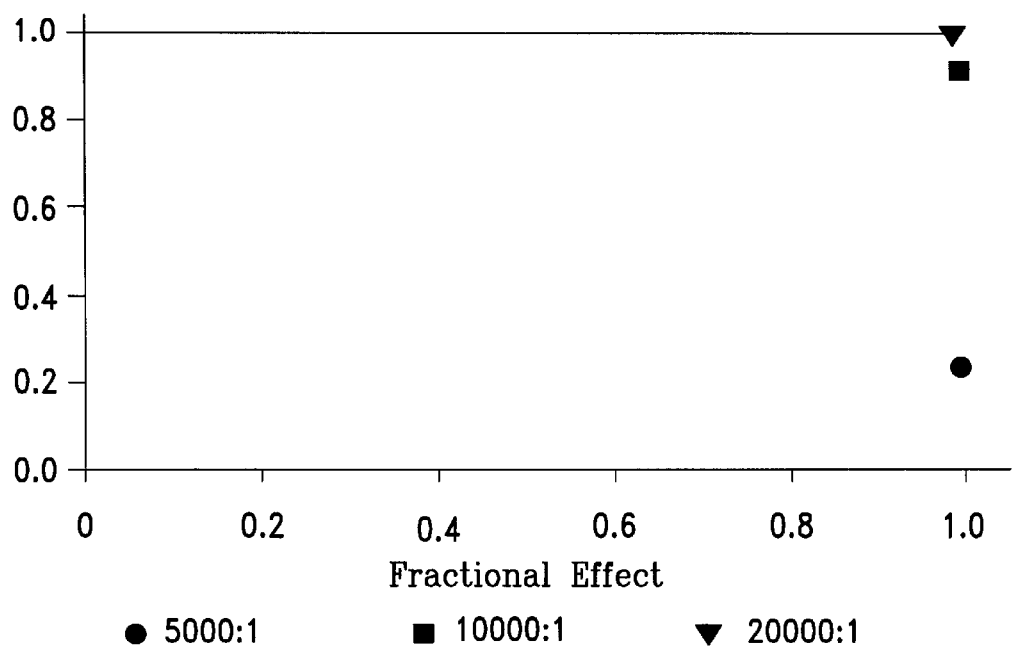

The synergistic effect of a combination of S-acetyl glutathione and ACV according to Table 1 is represented in diagrammatic form in FIGS. 1A and 1B, according to a known mathematical model.

FIG. 1A relates to the concentration of S-acetyl glutathione of 20 mM, and FIG. 1B to the concentration of 10 mM. Points are entered in a co-ordinate system for the various different concentration ratios of S-acetyl glutathione to ACV, with the exception of the significant case of 20 mM/2 $\mu$M, the Y-axis of the said co-ordinate system reproducing the combination index. With the evaluation model used, a combination index of less than 1 signifies a synergistic effect, a combination index equal to 1 an additive effect, and a combination index of greater than 1 an antagonistic effect. It can be seen that all the combinations used lie in the synergistic range.

In-vitro experiments were also conducted on the influence of S-acetyl glutathione and Aciclovir (ACV), in each case individually and in combination with one another, on the VZV (Strain 4400/95) replication in retinal pigments epithelium cells (RPE) with UMDM plus 10% foetal calf serum as the medium. The results are reproduced in Table 2.

At a concentration of 10 mM, S-acetyl glutathione together with ACV in three different concentrations shows a marked synergistic effect, which is highest at a concentration of the ACV of 40 mM. With this combination, the number of plaques or holes which occur under the influence of the VZV drops below the limit of demonstrability.

Figure 2:
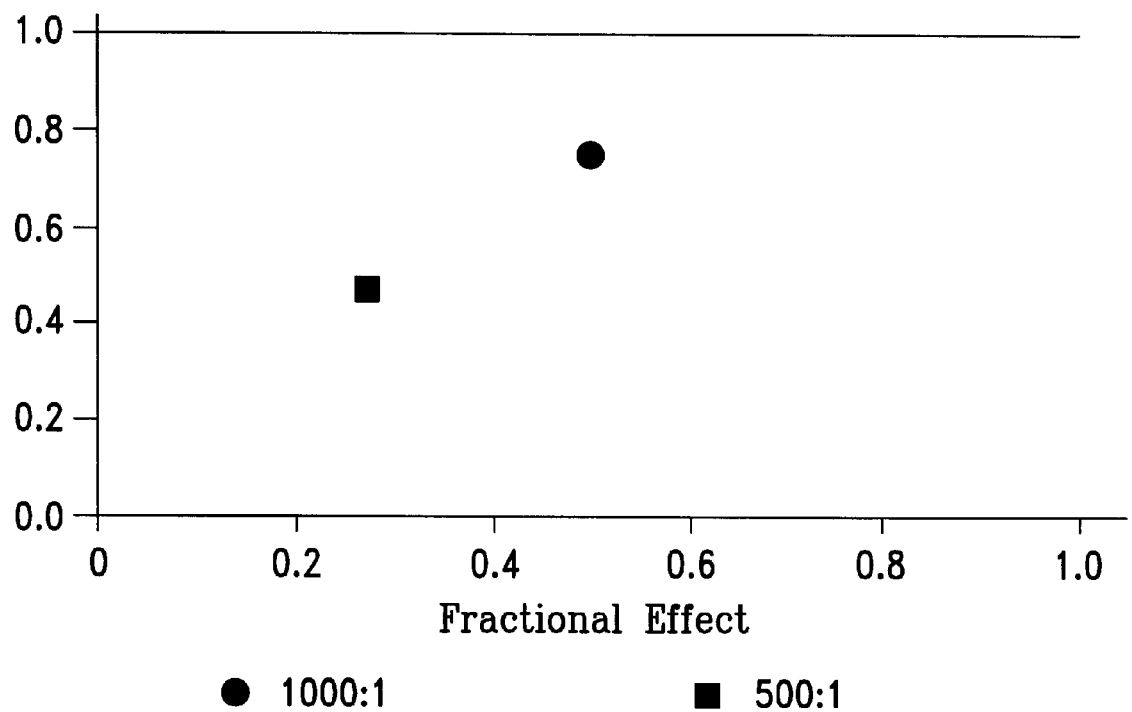
FIG. 2 is a diagram showing the results of experiments as to the influence of s-acetyl glutathione and Aciclovir (ACV) on retinal pigmented epithelium cells (REP)

FIG. 2 shows the synergistic effect according to Table 2 using the same model as was used for FIGS. 1A and 1B.

A pharmaceutical substance against the Herpes Simplex virus contains the two substances S-acetyl glutathione and ACV, for preference on a cream or salve base, for external application and in the concentrations which have proved to be particularly effective according to the experiments described heretofore.

TABLE 1

Influence of S-acetyl glutathione and Aciclovir (ACV) individually or in combination on HSV-1 (McIntyre Strain) replication in cultures of human fibroblasts

| S-acetyl glutathione (mM) | ACV ($\mu$M) | Virus titre (TCID$_{60}$/ml) | Reduction factor | Combination effect |
|---|---|---|---|---|
| | | 2.1 × 10$^7$ | 1.0 | |
| 20 | | 2.4 × 10$^5$ | 91 | |
| 10 | | 1.5 × 10$^6$ | 14 | |
| | 2 | 3.8 × 10$^3$ | 5526 | |
| | 1 | 3.3 × 10$^5$ | 64 | |
| | 0.5 | 3.1 × 10$^6$ | 6.8 | |
| 20 | 2 | not measurable | ∞ | Synergistic |
| 20 | 1 | 2.3 × 10$^2$ | 91304 | Synergistic |
| 20 | 0.5 | 9.2 × 10$^3$ | 2283 | Synergistic |
| 10 | 2 | 6.7 × 10$^6$ | 313433 | Synergistic |
| 10 | 1 | 2.4 × 10$^4$ | 875 | Synergistic |
| 10 | 0.5 | 1.3 × 10$^5$ | 160 | Synergistic |

TABLE 2

Influence of S-acetyl glutathione and Aciclovir (ACV) individually or in combination on VZV (Strain 4400/95) replication in retinal pigmented epithelium cells (RPE)

| S-acetyl glutathione (mM) | ACV ($\mu$M) | Plaque number (%) | Combination effect |
|---|---|---|---|
| 10 | | 59 | |
| 20 | | 52 | |
| | 10 | 88 | |
| | 20 | 81 | |
| | 40 | 26 | |

TABLE 2-continued

Influence of S-acetyl glutathione and Aciclovir (ACV) individually or in combination on VZV (Strain 4400/95) replication in retinal pigmented epithelium cells (RPE)

| S-acetyl glutathione (mM) | ACV ($\mu$M) | Plaque number (%) | Combination effect |
|---|---|---|---|
| 10 | 10 | 50 | Synergistic |
| 10 | 20 | 27 | Synergistic |
| 10 | 40 | not measurable | Synergistic |

What is claimed is:

1. A substance mixture containing S-acetyl glutathione and Aciclovir as medication against the Herpes Simplex virus or the Varicella Zoster virus.

2. A method of treating a human or animal body against infection with the Herpes Simplex virus and the Varicella Zoster virus, comprising administering S-acetyl glutathione in combination with Aciclovir to said human or animal body.

* * * * *